United States Patent [19]

Lesher et al.

[11] 4,391,811

[45] Jul. 5, 1983

[54] 2-AMINO-6-(PYRIDINYL)-3H-IMIDAZO[4,5-b]PYRIDINES AND THEIR CARDIOTONIC USE

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 307,777

[22] Filed: Oct. 2, 1981

[51] Int. Cl.³ ................... C07D 487/04; A61K 31/44
[52] U.S. Cl. ................................ 424/263; 546/118
[58] Field of Search ................. 546/118; 424/256, 263

[56] References Cited

U.S. PATENT DOCUMENTS 3,920,669  11/1975  Kristinsson et al. ............... 546/118
3,954,438   5/1976  Hunter et al. ........................ 71/92

OTHER PUBLICATIONS

Chemical Abstracts, 89:43341s (1978).

Baldwin et al., [J. Med. Chem. 20, 1189–1193 (1977)].

*Primary Examiner*—Norma S. Milestone
*Attorney, Agent, or Firm*—Robert K. Bair; B. Woodrow Wyatt; Paul Dupont

[57] ABSTRACT

2-(NB)-3-R-6-PY-5-Q-3H-imidazo[4,5-b]pyridines (I) and salts, useful as cardiotonics, where NB is amino or dimethylamino, R is lower-alkyl, Q is hydrogen or lower-alkyl, and PY is 4- or 3-pyridinyl or 4- or 3-pyridinyl having one or two lower-alkyl substituents, are prepared by reacting a 2-RNH-3-amino-5-PY-6-Q-pyridine with a di-(lower-alkyl) 2-methylthiopseudourea-1,3-dicarboxylate to produce 2-carbo(lower-alkoxy)amino-3-R-6-PY-5-Q-3H-imidazo[4,5-b] pyridine and hydrolyzing the latter to produce I where NB is amino and by reacting a 2-RNH-3-amino-5-PY-6-Q-pyridine with dichloromethylene-N,N-dimethylammonium chloride to produce I where NB is dimethylamino. Cardiotonic use of I is disclosed and claimed.

10 Claims, No Drawings

2-AMINO-6-(PYRIDINYL)-3H-IMIDAZO[4,5-b]PYRIDINES AND THEIR CARDIOTONIC USE

CROSS-REFERENCE TO RELATED APPLICATION

Lesher, Opalka and Page application Ser. No. 135,211, filed Mar. 28, 1980 and now U.S. Pat. No. 4,276,293, issued June 30, 1981, shows inter alia 2-$R_2$-3-(lower-alkyl)-6-(pyridinyl)-5-Q-3H-imidazo[4,5-b]pyridines, their use as cardiotonics and their preparation by reacting a 2-(lower-alkylamino)-3-amino-5-(pyridinyl)-6-Q-pyridine with a tri-(lower-alkyl) ortho-(lower-alkanoate), where $R_2$ and Q are each hydrogen or lower-alkyl.

BACKGROUND OF THE INVENTION (a) Field of the Invention

This invention relates to substituted 3H-imidazo[4,5-b]pyridines, their preparation and their use as cardiotonics.

(b) Description of the Prior Art

Baldwin et al. [J. Med. Chem. 20, 1189–1193 (1977)] disclose the preparation of 2-(3-pyridinyl)-1H-imidazo[4,5-b]pyridine and 2-(4-pyridinyl)-1H-imidazo[4,5-b]pyridine by heating, respectively, a mixture of 2,3-diaminopyridine and nicotinic acid and a mixture of 2,3-diaminopyridine and isonicotinic acid. Both of these compounds were reported by Baldwin et al. to be inactive when tested as inhibitors of xanthine oxidase.

SUMMARY OF THE INVENTION

In a composition of matter aspect, the invention relates to 2-(NB)-3-R-6-PY-5-Q-3H-imidazo[4,5-b]pyridines and acid-addition salts thereof, which are useful as cardiotonic agents, where NB, R, PY and Q have the meanings given hereinbelow.

The invention in a process aspect comprises reacting 2-RNH-3-amino-5-PY-6-Q-pyridine with a di-(lower-alkyl) 2-methylthiopseudourea-1,3-dicarboxylate to produce 2-carbo(lower-alkoxy)amino-3-R-6-PY-5-Q-3H-imidazo[4,5-b]pyridine and hydrolyzing the latter to produce 2-amino-3-R-6-PY-5-Q-3H-imidazo[4,5-b]pyridine.

The invention in another process aspect comprises reacting 2-RNH-3-amino-5-PY-6-Q-pyridine with dichloromethylene-N,N-dimethylammonium chloride to produce 2-dimethylamino-3-R-6-PY-5-Q-3H-imidazo[4,5-b]pyridine.

A composition aspect of the invention relates to a cardiotonic composition for increasing cardiac contractility in a patient, said composition comprising a pharmaceutically acceptable carrier and, as the active ingredient thereof, a cardiotonically effective amount of 2-(NB)-3-R-6-PY-5-Q-3H-imidazo[4,5-b]pyridine or pharmaceutically acceptable acid-addition salt thereof.

In a method aspect, the invention relates to a method for increasing cardiac contractility in a patient requiring such treatment which comprises the administration of a medicament comprising a pharmaceutically acceptable carrier and, as the active component thereof, a cardiotonically effective amount of 2-(NB)-3-R-6-PY-5-Q-3H-imidazo[4,5-b]pyridine or pharmaceutically acceptable acid-addition salt thereof.

DETAILED DESCRIPTION INCLUSIVE OF PREFERRED EMBODIMENTS

In a composition of matter aspect the invention resides in a 2-(NB)-3-R-6-PY-5-Q-3H-imidazo[4,5-b]pyridine having formula I

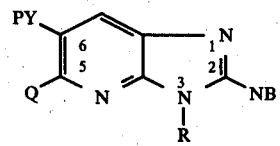

where Q is hydrogen or lower-alkyl, R is lower-alkyl, NB is amino or dimethylamino, and PY is 4- or 3-pyridinyl or 4- or 3-pyridinyl having one or two lower-alkyl substituents, or acid-addition salts thereof. The compounds of formula I and said salts are useful as cardiotonic agents, as determined by standard pharmacological evaluation procedures. Preferred embodiments are those of formula I where PY is 4-pyridinyl or 3-pyridinyl, Q is hydrogen, methyl or ethyl, and R is methyl or ethyl. Particularly preferred embodiments are those where PY is 4-pyridinyl, Q is hydrogen, R is methyl and NB is amino or dimethylamino.

In one process aspect the invention resides in the process which comprises reacting 2-RNH-3-amino-5-PY-6-Q-pyridine with a di-(lower-alkyl) 2-methylthiopseudourea-1,3-dicarboxylate of formula II

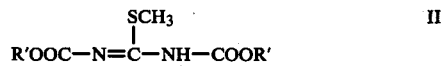

where R' is lower-alkyl, to produce 2-carbo(lower-alkoxy)-amino-3-R-6-PY-5-Q-3H-imidazo[4,5-b]pyridine and hydrolyzing the latter compound to produce 2-amino-3-R-6-PY-5-Q-3H-imidazo[4,5-b]pyridine of formula I where NB is amino. Preferred and particularly preferred embodiments of this process aspect are those which produce the above-said respective preferred and particularly preferred composition of matter embodiments of formula I and which utilize dimethyl 2-methylthiopseudourea-1,3-dicarboxylate (formula II, R' is methyl) in the first step.

In another process aspect the invention resides in the process which comprises reacting 2-RNH-3-amino-5-PY-6-Q-pyridine with dichloromethylene-N,N-dimethylammonium chloride of formula III

to produce 2-dimethylamino-3-R-6-PY-5-Q-3H-imidazo[4,5-b]pyridine of formula I where NB is dimethylamino. Preferred and particularly preferred embodiments of this process aspect are those which produce the above-said respective preferred and particularly preferred composition of matter embodiments of formula I.

A composition aspect of the invention resides in a cardiotonic composition for increasing cardiac contractility, said composition comprising a pharmaceutically acceptable carrier and, as the active component thereof, a cardiotonically effective amount of 2-(NB)-3-R-6-PY-5-Q-3H-imidazo[4,5-b]pyridine of formula I or pharmaceutically acceptable acid-addition salt thereof. Preferred and particularly preferred embodiments are those having as active components the above-said preferred and particularly preferred embodiments of formula I.

A method aspect of the invention resides in the method for increasing cardiac contractility in a patient requiring such treatment which comprises administering orally or parenterally in a solid or liquid dosage form to such patient a cardiotonically effective amount of 2-(NB)-3-R$_3$-6-PY-5-Q-3H-imidazo[4,5-b]pyridine of formula I, where PY, R, NB and Q are defined as in formula I, or pharmaceutically acceptable acid-addition salts thereof. Preferred and particularly preferred embodiments of this method aspect are those using the preferred and particularly preferred cardiotonics of formula I noted above.

The term "lower-alkyl" as used herein, e.g., as one of the meanings for Q or as the meaning for R or R' or as a substituent for PY in formula I, means alkyl radicals having from one to four carbon atoms which can be arranged as straight or branched chains, illustrated by methyl, ethyl, n-propyl, isopropyl, n-butyl, sec.-butyl, tert.-butyl, isobutyl, and the like.

Illustrative of PY in formula I where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form or the hydrochloride salt; however, appropriate pharmaceutically acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compound (I) are preferred, all acid-addition salts are within the scope of our invention. All acid-addition salts are useful as sources of the free base form even if the particular salt per se is desired only as an intermediate product, as for example when the salt is formed only for purposes of purification or identification, or when it is used as an intermediate in preparing a pharmaceutically acceptable salt by ion exchange procedures.

The molecular structure of the compounds of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The preparation of 2-carboalkoxyamino-3-R-6-PY-5-Q-3H-imidazo[4,5-b]pyridine by reacting 2-RNH-3-amino-5-PY-6-Q-pyridine with a di-(lower-alkyl) 2-methylthiopseudourea-1,3-dicarboxylate, preferably where lower-alkyl is methyl, is carried out by heating the reactants at about 65° C. to about 135° C., preferably about 85° C. to about 115° C., in a suitable solvent inert under the reaction conditions. The reaction was conveniently run by heating the reactants on a steam bath in water containing acetic acid. Other suitable solvents include a lower-alkanol, e.g., methanol, ethanol, preferably containing a suitable acid, e.g., acetic acid, hydrochloric acid.

The intermediate 2-RNH-3-amino-5-PY-6-Q-pyridines and their preparation are shown in said U.S. Pat. No. 4,276,293.

The intermediate di-(lower-alkyl) 2-methylthiopseudourea-1,3-dicarboxylates are known and are readily prepared by reacting 2-methyl-2-thiopseudourea sulfate with a lower-alkyl chloroformate, e.g., U.S. Pat. Nos. 2,933,504, issued Apr. 19, 1960 and 3,812,173, issued May 21, 1974.

The hydrolysis of 2-carboalkoxyamino-3-R-6-PY-5-Q-3H-imidazo[4,5-b]pyridine is carried out by heating it with an aqueous mineral acid, preferably aqueous hydrochloric acid. The hydrolysis is run by heating the reactants at about 70° C. to about 130° C., preferably at about 90° C. to about 110° C. Alternatively, this hydrolysis can be run using aqueous sodium or potassium hydroxide instead of aqueous mineral acid.

The preparation of 2-dimethylamino-3-R-6-PY-5-Q-3H-imidazo[4,5-b]pyridine by reacting 2-RNH-3-amino-5-PY-6-Q-pyridine with dichloromethylene-N,N-dimethylammonium chloride is carried out by heating the reactants in a suitable inert solvent at about 60° C. to about 220° C., preferably about 100° C. to 200° C. The reaction was conveniently run in tetramethylurea at about 200° C. Other suitable solvents include dioxane, chloroform (longer reaction time), and the like.

The following examples will further illustrate the invention without, however, limiting it thereto.

A.
2-AMINO-3-R-6-PY-5-Q-3H-IMIDAZO[4,5-b]PYRIDINES

A-1. 2-Amino-3-methyl-6-(4-pyridinyl)-3H-imidazo[4,5-b]pyridine

A mixture containing 24 g. of 3-amino-2-methylamino-5-(4-pyridinyl)pyridine, 28.8 g. of dimethyl 2-methylthiopseudourea-1,3-dicarboxylate, 10 ml. of acetic acid and 300 ml. of water was heated on a steam bath for four hours and then allowed to stand at room temperature overnight. The reaction mixture was made basic with ammonium hydroxide. The separated solid was collected by filtration, washed with water, dried and then combined with additional solid product obtained from the basic mother liquor as follows. The basic mother liquor was evaporated to dryness in vacuo; the residue treated twice with water, each time decanting the water, and then was treated with about 100 ml. of ethanol; the mixture cooled; and, the solid collected by filtration. The solid was washed with ether, dried and combined, as noted above, with the collected solid that had separated from the basic reaction mixture. The combined solids, 18 g. of 2-carbomethoxyamino-3-methyl-6-(4-pyridinyl)-3H-imidazo[4,5-b]pyridine, without further purification, was combined with 200 ml. of 6 N aqueous hydrochloric acid and the mixture heated overnight. Another 100 ml. of 6 N HCl was added and heating was continued overnight. The reaction mixture was evaporated in vacuo to dryness, the residue was dissolved in water and the solution was neutralized with ammonium hydroxide. The separated solid was collected, washed with water, dried, recrystallized twice from dimethylformamide, washed successively with ethanol and ether, and dried to yield 8.5 g. of 2-amino-3-methyl-6-(4-pyridinyl)-3H-imidazo[4,5-b]pyridine, m.p. >300° C.

Acid-addition salts of 2-amino-3-methyl-6-(4-pyridinyl)-3H-imidazo[4,5-b]pyridine are conveniently prepared by adding to a mixture of 5 g. of 2-amino-3-methyl-6-(4-pyridinyl)-3H-imidazo[4,5-b]pyridine in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 2-amino-3-methyl-6-(4-pyridinyl)-3H-imidazo[4,5-b]pyridine and the appropriate acid, e.g., lactic acid or hydrochloric acid, to prepare respectively the monolactate or monohydrochloride salt in aqueous solution.

Following the procedure described in Example A-1 but using in place of 3-amino-2-methylamino-5-(4-pyridinyl)pyridine a molar equivalent quantity of the appropriate 3-amino-2-RNH-5-PY-6-Q-pyridine, it is contemplated that there can be obtained the corresponding 2-amino-3-R-6-PY-5-Q-3H-imidazo[4,5-b]pyridines of Examples A-2 through A-9.

A-2. 2-Amino-3-ethyl-6-(4-pyridinyl)-3H-imidazo[4,5-b]pyridine, using 3-amino-2-ethylamino-5-(4-pyridinyl)pyridine.
A-3. 2-Amino-3-n-propyl-6-(3-pyridinyl)-3H-imidazo[4,5-b]pyridine, using 3-amino-2-n-propylamino-5-(3-pyridinyl)pyridine.
A-4. 2-Amino-3-isopropyl-6-(2-methyl-5-pyridinyl)-3H-imidazo[4,5-b]pyridine, using 3-amino-2-isopropylamino-5-(2-methyl-5-pyridinyl)pyridine.
A-5. 2-Amino-3-n-butyl-6-(5-methyl-3-pyridinyl)-3H-imidazo[4,5-b]pyridine, using 3-amino-2-n-butylamino-5-(5-methyl-3-pyridinyl)pyridine.
A-6. 2-Amino-3,5-dimethyl-6-(4-pyridinyl)-3H-imidazo[4,5-b]pyridine, using 3-amino-6-methyl-2-methylamino-5-(4-pyridinyl)pyridine.
A-7. 2-Amino-5-ethyl-3-methyl-6-(4-pyridinyl)-3H-imidazo[4,5-b]pyridine, using 3-amino-6-ethyl-2-methylamino-5-(4-pyridinyl)pyridine.
A-8. 2-Amino-5-isopropyl-3-methyl-6-(4-pyridinyl)-3H-imidazo[4,5-b]pyridine, using 3-amino-6-isopropyl-2-methylamino-5-(4-pyridinyl)pyridine.
A-9. 2-Amino-5-n-butyl-3-methyl-6-(4-pyridinyl)-3H-imidazo[4,5-b]pyridine, using 3-amino-6-n-butyl-2-methylamino-5-(4-pyridinyl)pyridine.

B.
2-DIMETHYLAMINO-3-R-6-PY-5-Q-3H-IMIDAZO[4,5-b]PYRIDINES

B-1. 2-Dimethylamino-3-methyl-6-(4-pyridinyl)-3H-imidazo[4,5-b]pyridine

A mixture containing 8.01 g. of 3-amino-2-methylamino-5-(4-pyridinyl)pyridine, 6.62 g. of dichloromethylene-N,N-dimethylammonium chloride and 400 ml. of dioxane was refluxed with stirring for seventeen hours. After tlc analysis (CHCl$_3$—CH$_3$OH) showed the presence of some starting material, another 0.65 g. of dichloromethylene-N,N-dimethylammonium chloride was added to the partly cooled reaction mixture and the resulting mixture was refluxed with stirring for an additional three hours. The reaction mixture was chilled and the solid was collected by filtration, washed with ether and dried at 90° C. in a vacuum oven to yield 12.61 g. of a tan solid, m.p. 268°-272° C. After tlc analysis of this solid again showed the presence of some starting material, the solid was combined with 6.28 g. of dichloromethylene-N,N-dimethylammonium chloride and 200 ml. of tetramethylurea and the mixture was refluxed with stirring for three hours and concentrated in vacuo to dryness. The residual brown solid was recrystallized from methanol-acetone while adding ethanolic hydrogen chloride to a pH of <6 to yield 12.17 g. of 2-dimethylamino-3-methyl-6-(4-pyridinyl)-3H-imidazo[4,5-b]pyridine dihydrochloride, m.p. 258°-260° C. This product was recrystallized from methanol (300 ml.)-acetone and dried at 90° C. in a vacuum oven to yield 9.12 g. of 2-dimethylamino-3-methyl-6-(4-pyridinyl)-3H-imidazo[4,5-b]pyridine dihydrochloride hydrate (4:1), m.p. 260°-265° C. with decomposition.

Other acid-addition salts of 2-dimethylamino-3-methyl-6-(4-pyridinyl)-3H-imidazo[4,5-b]pyridine are conveniently prepared by adding to a mixture of 2 g. of 2-dimethylamino-3-methyl-6-(4-pyridinyl)-3H-imidazo[4,5-b]pyridine in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 2-dimethylamino-3-methyl-6-(4-pyridinyl)-3H-imidazo[4,5-b]pyridine and the appropriate acid, e.g., lactic acid or hydrochloric acid, to prepare respectively the monolactate or monohydrochloride salt in aqueous solution.

Following the procedure described in Example B-1 but using in place of 3-amino-2-methylamino-5-(4-pyridinyl)-pyridine a molar equivalent quantity of the appropriate 3-amino-2-RNH-5-PY-6-Q-pyridine, it is contemplated that there can be obtained the corresponding 2-dimethylamino-3-R-6-PY-5-Q-3H-imidazo[4,5-b]pyridines of Examples B-2 through B-9.

B-2. 2-Dimethylamino-3-ethyl-6-(4-pyridinyl)-3H-imidazo[4,5-b]pyridine, using 3-amino-2-ethylamino-5-(4-pyridinyl)pyridine.

B-3. 2-Dimethylamino-3-n-propyl-6-(3-pyridinyl)-3H-imidazo[4,5-b]pyridine, using 3-amino-2-n-propylamino-5-(3-pyridinyl)pyridine.

B-4. 2-Dimethylamino-3-isopropyl-6-(2-methyl-5-pyridinyl)-3H-imidazo[4,5-b]pyridine, using 3-amino-2-isopropylamino-5-(2-methyl-5-pyridinyl)pyridine.

B-5. 2-Dimethylamino-3-n-butyl-6-(5-methyl-3-pyridinyl)-3H-imidazo[4,5-b]pyridine, using 3-amino-2-n-butylamino-5-(5-methyl-3-pyridinyl)pyridine.

B-6. 2-Dimethylamino-3,5-dimethyl-6-(4-pyridinyl)-3H-imidazo[4,5-b]pyridine, using 3-amino-6-methyl-2-methylamino-5-(4-pyridinyl)pyridine.

B-7. 2-Dimethylamino-5-ethyl-3-methyl-6-(4-pyridinyl)-3H-imidazo[4,5-b]pyridine, using 3-amino-6-ethyl-2-methylamino-5-(4-pyridinyl)pyridine.

B-8. 2-Dimethylamino-5-isopropyl-3-methyl-6-(4-pyridinyl)-3H-imidazo[4,5-b]pyridine, using 3-amino-6-isopropyl-2-methylamino-5-(4-pyridinyl)pyridine.

B-9. 2-Dimethylamino-5-n-butyl-3-methyl-6-(4-pyridinyl)-3H-imidazo[4,5-b]pyridine, using 3-amino-6-n-butyl-2-methylamino-5-(4-pyridinyl)pyridine.

The usefulness of the compounds of formula I or salts thereof as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with lower or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I or pharmaceutically acceptable acid-addition salts thereof at a dose of 100 µg/ml., were found to cause significant increases, that is, greater than 25% (cat) or 30% (g. pig) in papillary muscle force and significant increases, that is, greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, the compound of Example A-1, namely, 2-amino-3-methyl-6-(4-pyridinyl)-3H-imidazo[4,5-b]pyridine, when tested by said cat atria and papillary muscle procedure was found to cause papillary muscle and right atrial force increases of 66% and 93% when tested at 100 µg/ml.; the compound of Example B-1, namely, 2-dimethylamino-3-methyl-6-(4-pyridinyl)-3H-imidazo[4,5-b]pyridine, when tested by said guinea pig atria and papillary muscle procedure was found to cause papillary muscle and right atrial force increases of 69% and 181% when tested at 100 µg/ml.

The present invention includes within its scope a cardiotonic composition for increasing cardiac contractility, said composition comprising a pharmaceutically acceptable carrier and, as the active component thereof, the cardiotonic 2-(NB)-3-R-6-PY-5-Q-3H-imidazo[4,5-b]pyridine of formula I or pharmaceutically acceptable acid-addition salt thereof. The invention also includes within its scope the method for increasing cardiac contractility in a patient requiring such treatment which comprises administering to such patient a cardiotonically effective amount of 2-(NB)-3-R-6-PY-5-Q-3H-imidazo[4,5-b]pyridine of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A 2-(NB)-3-R-6-PY-5-Q-3H-imidazo[4,5-b]pyridine having the formula

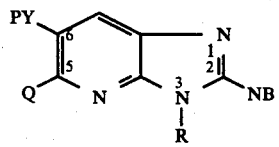

where Q is hydrogen or lower-alkyl, R is lower-alkyl, NB is amino or dimethylamino, and PY is 4- or 3-pyridinyl or 4- or 3-pyridinyl having one or two lower-alkyl substituents, or acid-addition salt thereof.

2. A compound according to claim 1 where PY is 4-pyridinyl or 3-pyridinyl, Q is hydrogen, methyl or ethyl and R is methyl or ethyl.

3. 2-Amino-3-methyl-6-(4-pyridinyl)-3H-imidazo[4,5-b]pyridine or acid-addition salt thereof.

4. 2-Dimethylamino-3-methyl-6-(4-pyridinyl)-3H-imidazo[4,5-b]pyridine or acid-addition salt thereof.

5. A cardiotonic composition for increasing cardiac contractility, said composition comprising a pharmaceutically acceptable inert carrier and, as the active component thereof, a cardiotonically effective amount of 2-(NB)-3-R-6-PY-5-Q-3H-imidazo[4,5-b]pyridine or pharmaceutically acceptable acid-addition salt thereof, where Q is hydrogen or lower-alkyl, R is lower-alkyl, NB is amino or dimethylamino, and PY is 4- or 3-pyridinyl or 4- or 3-pyridinyl having one or two lower-alkyl substituents.

6. A composition according to claim 5 where the active component is 2-amino-3-methyl-6-(4-pyridinyl)-3H-imidazo[4,5-b]pyridine or acid-addition salt thereof.

7. A composition according to claim 5 where the active component is 2-dimethylamino-3-methyl-6-(4-pyridinyl)-3H-imidazo[4,5-b]pyridine or acid-addition salt thereof.

8. The method for increasing cardiac contractility in a patient requiring such treatment which comprises administering orally or parenterally in a solid or liquid dosage form to such patient a cardiotonically effective amount of 2-(NB)-3-R-6-PY-5-Q-3H-imidazo[4,5-b]pyridine or pharmaceutically acceptable acid-addition salt thereof, where Q is hydrogen or lower-alkyl, R is lower-alkyl, NB is amino or dimethylamino, and PY is 4- or 3-pyridinyl or 4- or 3-pyridinyl having one or two lower-alkyl substituents.

9. A method according to claim 8 where the active component is 2-amino-3-methyl-6-(4-pyridinyl)-3H-imidazo[4,5-b]pyridine or acid-addition salt thereof.

10. A method according to claim 8 where the active component is 2-dimethylamino-3-methyl-6-(4-pyridinyl)-3H-imidazo[4,5-b]pyridine or acid-addition salt thereof.

* * * * *